United States Patent
Smyth et al.

(10) Patent No.: US 11,185,486 B2
(45) Date of Patent: Nov. 30, 2021

(54) PERSONAL CLEANSING COMPOSITIONS AND METHODS

(71) Applicant: The Procter & Gamble Company, Cincinnati, OH (US)

(72) Inventors: Kelsey Marie Smyth, Cincinnati, OH (US); Edward Dewey Smith, III, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/299,722

(22) Filed: Oct. 21, 2016

(65) Prior Publication Data
US 2018/0110709 A1   Apr. 26, 2018

(51) Int. Cl.
| | |
|---|---|
| *C11D 1/14* | (2006.01) |
| *C11D 1/90* | (2006.01) |
| *C11D 1/94* | (2006.01) |
| *C11D 3/22* | (2006.01) |
| *A61K 8/44* | (2006.01) |
| *A61Q 19/10* | (2006.01) |
| *A61Q 5/02* | (2006.01) |
| *A61K 8/34* | (2006.01) |
| *A61K 8/46* | (2006.01) |
| *A61K 8/06* | (2006.01) |
| *A61K 8/73* | (2006.01) |
| *A61Q 13/00* | (2006.01) |
| *C11D 1/29* | (2006.01) |
| *C11D 3/50* | (2006.01) |

(Continued)

(52) U.S. Cl.
CPC .............. *A61K 8/442* (2013.01); *A61K 8/068* (2013.01); *A61K 8/345* (2013.01); *A61K 8/463* (2013.01); *A61K 8/731* (2013.01); *A61Q 5/02* (2013.01); *A61Q 13/00* (2013.01); *A61Q 19/10* (2013.01); *C11D 1/14* (2013.01); *C11D 1/29* (2013.01); *C11D 1/90* (2013.01); *C11D 1/94* (2013.01); *C11D 3/2041* (2013.01); *C11D 3/222* (2013.01); *C11D 3/43* (2013.01); *C11D 3/50* (2013.01)

(58) Field of Classification Search
CPC .... C11D 1/14; C11D 1/29; C11D 1/90; C11D 1/94; C11D 3/222; C11D 3/50; C11D 3/2041; C11D 3/43; C11D 17/0021
USPC ....... 510/101, 123, 124, 125, 127, 130, 136, 510/137, 138, 417, 473, 501, 505, 506
See application file for complete search history.

(56) References Cited

U.S. PATENT DOCUMENTS

| | | | |
|---|---|---|---|
| 2,438,091 | A | 3/1948 | Lynch |
| 2,528,378 | A | 10/1950 | Mannheimer |
| 2,658,072 | A | 11/1953 | Kosmin |

(Continued)

FOREIGN PATENT DOCUMENTS

| | | |
|---|---|---|
| CA | 2110951 A1 | 6/1994 |
| CA | 2196774 A1 | 2/1996 |

(Continued)

OTHER PUBLICATIONS

Dow—Personal Care Solutions, Cellulosic Thickeners Product Selection Guide, p. 1-2, Feb. 2015.*

(Continued)

*Primary Examiner* — Gregory R Delcotto
(74) *Attorney, Agent, or Firm* — Alexandra S. Anoff

(57) ABSTRACT

Rinse-off cleansing compositions can include surfactant, perfume, solvent, thickener, and water.

21 Claims, 2 Drawing Sheets

Figure 1:
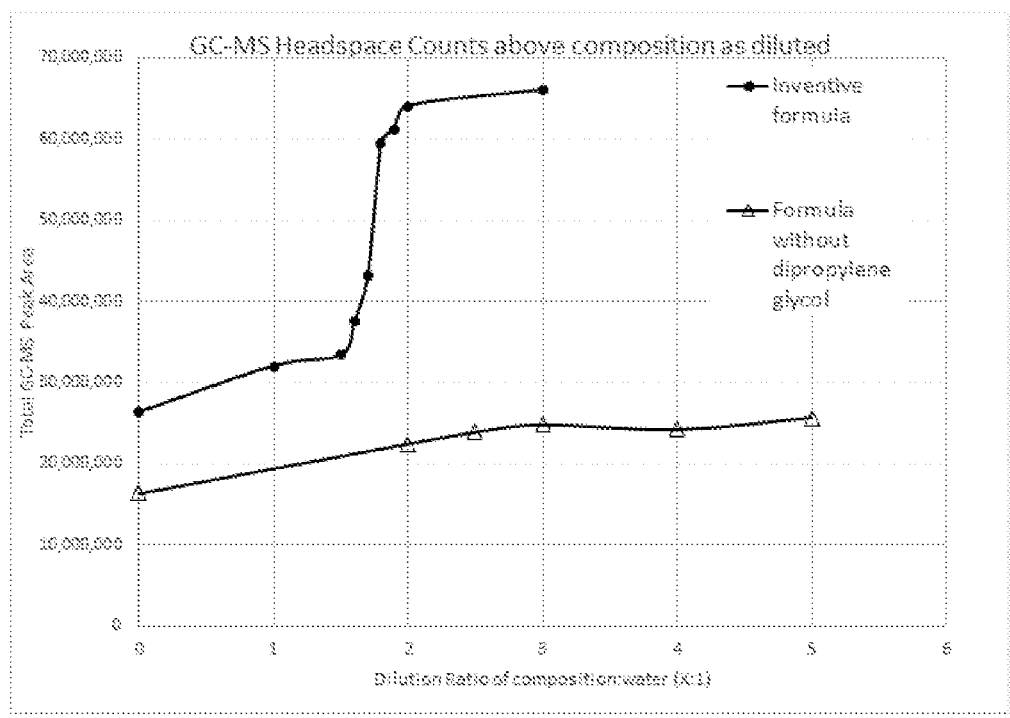
Figure 2:
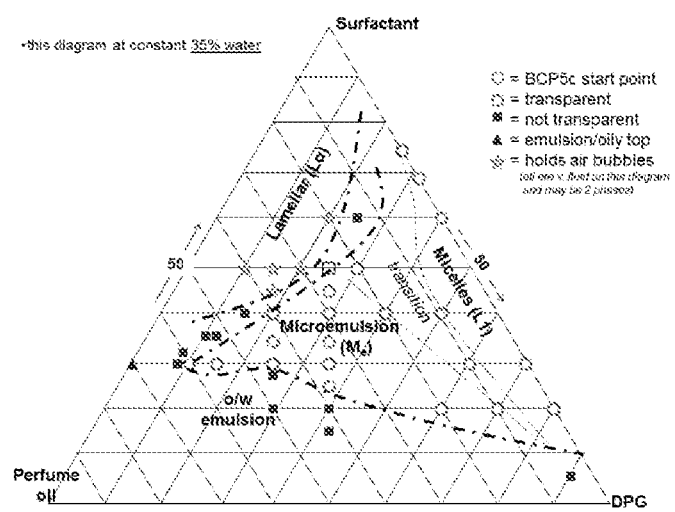
Figure 3:
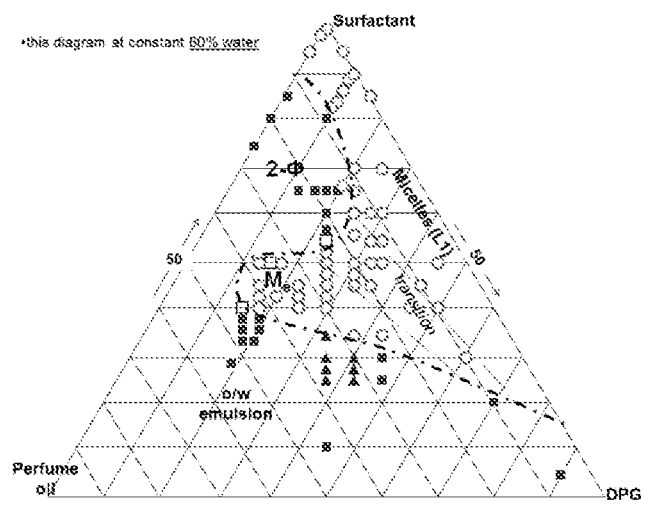

(51) Int. Cl.
*C11D 3/43* (2006.01)
*C11D 3/20* (2006.01)

(56) References Cited

U.S. PATENT DOCUMENTS

| | | | |
|---|---|---|---|
| 2,758,072 A | 8/1956 | Sutherland | |
| 3,962,150 A | 6/1976 | Viola | |
| 4,728,006 A | 3/1988 | Drobish | |
| 4,747,977 A | 5/1988 | Whitehead et al. | |
| 4,997,641 A | 3/1991 | Hartnett | |
| 5,104,646 A | 4/1992 | Bolich, Jr. et al. | |
| 5,106,609 A | 4/1992 | Bolich, Jr. et al. | |
| 5,106,613 A | 4/1992 | Hartnett | |
| 5,252,555 A | 10/1993 | Dartnell et al. | |
| 5,308,526 A | 5/1994 | Dias et al. | |
| 5,346,639 A | 9/1994 | Hatfield | |
| 5,374,614 A | 12/1994 | Behan | |
| 5,409,630 A | 4/1995 | Lysy et al. | |
| 5,415,857 A | 5/1995 | Robbins et al. | |
| 5,449,763 A | 9/1995 | Wulff | |
| 5,468,725 A | 11/1995 | Guenin et al. | |
| 5,507,970 A | 4/1996 | Ishikawa et al. | |
| 5,580,848 A | 12/1996 | Drapier | |
| 5,585,343 A | 12/1996 | Mcgee | |
| 5,597,792 A | 1/1997 | Klier | |
| 5,747,436 A | 5/1998 | Patel et al. | |
| 5,804,538 A | 9/1998 | Wei | |
| 5,839,614 A | 11/1998 | Brown | |
| 5,977,036 A | 11/1999 | Guskey | |
| 6,048,834 A | 4/2000 | Drapier et al. | |
| 6,074,996 A | 6/2000 | Elliott | |
| 6,107,261 A | 8/2000 | Taylor | |
| 6,136,771 A | 10/2000 | Taylor | |
| 6,204,230 B1 | 3/2001 | Taylor et al. | |
| 6,268,330 B1 | 7/2001 | Leonard et al. | |
| 6,271,187 B1 | 8/2001 | Hodge et al. | |
| 6,303,109 B1 | 10/2001 | Foerster et al. | |
| 6,329,331 B1 | 12/2001 | Aronson et al. | |
| 6,358,906 B1 | 3/2002 | Ochs | |
| 6,362,155 B1 | 3/2002 | Kinscherf | |
| 6,405,901 B1 | 6/2002 | Schantz | |
| 6,429,177 B1 | 8/2002 | Williams | |
| 6,440,907 B1 | 8/2002 | Santora et al. | |
| 6,491,933 B2 | 12/2002 | Lorenzi | |
| 6,806,249 B2 | 10/2004 | Yang | |
| 6,936,578 B2 | 8/2005 | Cordellina | |
| 6,977,082 B2 | 12/2005 | Seitz, Jr. et al. | |
| 6,998,382 B2 | 2/2006 | Yang | |
| 7,094,739 B2 | 8/2006 | Kessler | |
| 7,115,535 B1 | 10/2006 | Smith, III | |
| 7,608,575 B2* | 10/2009 | Panandiker | C11D 3/373 |
| | | | 510/276 |
| 7,704,932 B2 | 4/2010 | Evans et al. | |
| 7,874,466 B2 | 1/2011 | Mcconville | |
| 7,879,780 B2 | 2/2011 | Tsaur | |
| 7,884,061 B1 | 2/2011 | Hermanson et al. | |
| 8,008,239 B2 | 8/2011 | Anantaneni | |
| 8,114,826 B1 | 2/2012 | Hermanson et al. | |
| 8,207,100 B1 | 6/2012 | Hermanson | |
| 8,207,101 B1 | 6/2012 | Yang | |
| 8,236,747 B2 | 8/2012 | Holzhauer | |
| 8,263,096 B2 | 9/2012 | Myers | |
| 8,408,432 B2 | 4/2013 | Delamare | |
| 8,461,099 B2 | 6/2013 | Fraser et al. | |
| 8,672,195 B2 | 3/2014 | Py | |
| 8,697,622 B2* | 4/2014 | Man | A61K 8/068 |
| | | | 510/214 |
| 8,840,871 B2 | 9/2014 | Wei | |
| 8,899,449 B2 | 12/2014 | Daansen | |
| 8,937,102 B2 | 1/2015 | Hessel | |
| 9,254,498 B2 | 2/2016 | Daansen | |
| 9,271,908 B2 | 3/2016 | Allef | |
| 9,849,309 B2 | 12/2017 | Bouzeloc | |
| 10,675,231 B2 | 6/2020 | Smyth | |
| 10,806,686 B2 | 10/2020 | Smyth | |
| 10,952,949 B2 | 3/2021 | Smith, III et al. | |
| 10,952,950 B2 | 3/2021 | Smith, III et al. | |
| 2001/0056049 A1 | 12/2001 | Aronson | |
| 2002/0034489 A1 | 3/2002 | Wiegland et al. | |
| 2003/0180246 A1 | 9/2003 | Frantz | |
| 2004/0074924 A1 | 4/2004 | Kuhn | |
| 2005/0019299 A1 | 1/2005 | Librizzi et al. | |
| 2005/0020468 A1 | 1/2005 | Frantz | |
| 2005/0042192 A1 | 2/2005 | Evans | |
| 2005/0250658 A1 | 11/2005 | Putman | |
| 2006/0035807 A1* | 2/2006 | Kasturi | A61K 8/44 |
| | | | 510/475 |
| 2006/0040834 A1 | 2/2006 | Hilliard, Jr. et al. | |
| 2006/0078525 A1 | 4/2006 | Tomokuni | |
| 2006/0084589 A1* | 4/2006 | Vlad | A61L 9/012 |
| | | | 510/417 |
| 2006/0183662 A1 | 8/2006 | Crotty et al. | |
| 2007/0027050 A1 | 2/2007 | Crotty et al. | |
| 2007/0093404 A1* | 4/2007 | Gross | C11D 3/2093 |
| | | | 510/407 |
| 2007/0110700 A1* | 5/2007 | Wells | A61K 8/0295 |
| | | | 424/70.21 |
| 2007/0114246 A1 | 5/2007 | Awbrey | |
| 2007/0289613 A1* | 12/2007 | Geary | A61K 8/463 |
| | | | 134/34 |
| 2008/0003247 A1 | 1/2008 | Shick et al. | |
| 2008/0032909 A1 | 2/2008 | De Buzzaccarini | |
| 2008/0118591 A1 | 5/2008 | Natsch | |
| 2008/0139434 A1 | 6/2008 | Basappa | |
| 2008/0153929 A1 | 6/2008 | Miyahara et al. | |
| 2009/0095775 A1 | 4/2009 | Domoy | |
| 2009/0155383 A1 | 6/2009 | Kitko | |
| 2009/0221463 A1 | 9/2009 | Kitko et al. | |
| 2009/0312224 A1 | 12/2009 | Yang | |
| 2010/0136175 A1 | 6/2010 | Skiff | |
| 2010/0285155 A1 | 11/2010 | Gilbard et al. | |
| 2011/0152146 A1 | 6/2011 | Denutte et al. | |
| 2011/0152147 A1 | 6/2011 | Smets | |
| 2011/0212879 A1 | 9/2011 | Madden | |
| 2011/0268778 A1 | 11/2011 | Dihora | |
| 2011/0269657 A1 | 11/2011 | Dihora | |
| 2011/0269658 A1 | 11/2011 | Dihora | |
| 2011/0277796 A1 | 11/2011 | Waiters et al. | |
| 2011/0280823 A1 | 11/2011 | Madden | |
| 2011/0281827 A1 | 11/2011 | Tamarkin et al. | |
| 2011/0287073 A1 | 11/2011 | Strauss | |
| 2012/0015009 A9 | 1/2012 | Taylor | |
| 2012/0091218 A1 | 4/2012 | Mikkelsen | |
| 2012/0114819 A1 | 5/2012 | Ragnarsson | |
| 2012/0208898 A1 | 8/2012 | Dong | |
| 2012/0212879 A1 | 8/2012 | Li | |
| 2012/0316095 A1 | 12/2012 | Wei | |
| 2013/0012601 A1 | 1/2013 | Hessel | |
| 2013/0029932 A1 | 1/2013 | Kachi et al. | |
| 2013/0045306 A1 | 2/2013 | De Cleir | |
| 2013/0053295 A1 | 2/2013 | Kinoshita et al. | |
| 2013/0075430 A1 | 3/2013 | Ragnarsson | |
| 2013/0230610 A1 | 9/2013 | Redmond et al. | |
| 2013/0267451 A1 | 10/2013 | Hardy | |
| 2014/0017386 A1 | 1/2014 | Ragnarsson | |
| 2014/0162979 A1 | 6/2014 | Palla-venkata | |
| 2014/0219946 A1 | 8/2014 | Hloucha et al. | |
| 2014/0263443 A1 | 9/2014 | Furusawa | |
| 2014/0371128 A1 | 12/2014 | Hotz et al. | |
| 2015/0057208 A1 | 2/2015 | Frantz | |
| 2015/0203799 A1 | 7/2015 | Bettiol et al. | |
| 2015/0237905 A1 | 8/2015 | Ragnarsson | |
| 2015/0272197 A1 | 10/2015 | Swain | |
| 2015/0298875 A1 | 10/2015 | Dagnelie | |
| 2015/0322374 A1 | 11/2015 | Tchakalova et al. | |
| 2015/0359725 A1 | 12/2015 | Glenn, Jr. | |
| 2015/0359726 A1 | 12/2015 | Glenn, Jr. | |
| 2015/0359727 A1 | 12/2015 | Glenn, Jr. | |
| 2015/0359728 A1 | 12/2015 | Glenn, Jr. | |
| 2016/0128917 A1 | 5/2016 | Wei | |
| 2016/0128927 A1 | 5/2016 | Wei et al. | |
| 2016/0143821 A1 | 5/2016 | Chang | |
| 2016/0167864 A1 | 6/2016 | De Cleir | |
| 2016/0309871 A1 | 10/2016 | Torres Rivera et al. | |

(56) References Cited

U.S. PATENT DOCUMENTS

| | | |
|---|---|---|
| 2016/0310369 A1 | 10/2016 | Thompson |
| 2016/0310370 A1 | 10/2016 | Zhao |
| 2016/0310371 A1 | 10/2016 | Zhao |
| 2016/0310372 A1 | 10/2016 | Glenn, Jr. |
| 2016/0310375 A1 | 10/2016 | Torres Rivera |
| 2016/0310376 A1 | 10/2016 | Torres Rivera |
| 2016/0310377 A1 | 10/2016 | Torres Rivera |
| 2016/0310386 A1 | 10/2016 | Smith, III et al. |
| 2016/0310387 A1 | 10/2016 | Smith, III et al. |
| 2016/0310388 A1 | 10/2016 | Smith, III et al. |
| 2016/0310389 A1 | 10/2016 | Thompson |
| 2016/0310390 A1 | 10/2016 | Smith, III et al. |
| 2016/0310391 A1 | 10/2016 | Smith, III et al. |
| 2016/0310392 A1 | 10/2016 | Smith, III et al. |
| 2016/0310393 A1 | 10/2016 | Chang |
| 2016/0310397 A1 | 10/2016 | Johnson |
| 2016/0310402 A1 | 10/2016 | Zhao |
| 2016/0354300 A1 | 12/2016 | Thompson |
| 2016/0374932 A1 | 12/2016 | Song |
| 2017/0087068 A1 | 3/2017 | Callens |
| 2017/0165155 A1 | 6/2017 | Glenn, Jr. |
| 2017/0165156 A1 | 6/2017 | Glenn, Jr. |
| 2017/0165157 A1 | 6/2017 | Glenn, Jr. |
| 2017/0165162 A1 | 6/2017 | Glenn, Jr. |
| 2017/0165163 A1 | 6/2017 | Glenn, Jr. |
| 2017/0165164 A1 | 6/2017 | Zhao et al. |
| 2017/0165165 A1 | 6/2017 | Zhao et al. |
| 2017/0165191 A1 | 6/2017 | Glenn, Jr. |
| 2017/0174413 A1 | 6/2017 | Callens |
| 2017/0246101 A1 | 8/2017 | Iwata |
| 2017/0278249 A1 | 9/2017 | Stofel et al. |
| 2017/0304172 A1 | 10/2017 | Chang |
| 2017/0304184 A1 | 10/2017 | Glenn, Jr. |
| 2017/0304185 A1 | 10/2017 | Glenn, Jr. |
| 2017/0304186 A1 | 10/2017 | Glenn, Jr. |
| 2018/0110688 A1 | 4/2018 | Torres Rivera |
| 2018/0110689 A1 | 4/2018 | Torres Rivera |
| 2018/0110690 A1 | 4/2018 | Torres Rivera et al. |
| 2018/0110691 A1 | 4/2018 | Torres Rivera |
| 2018/0110692 A1 | 4/2018 | Torres Rivera |
| 2018/0110693 A1 | 4/2018 | Renock |
| 2018/0110694 A1 | 4/2018 | Renock |
| 2018/0110695 A1 | 4/2018 | Thompson et al. |
| 2018/0110696 A1 | 4/2018 | Johnson |
| 2018/0110697 A1 | 4/2018 | Smith, III |
| 2018/0110704 A1 | 4/2018 | Zhao |
| 2018/0110707 A1 | 4/2018 | Zhao |
| 2018/0110710 A1 | 4/2018 | Zhao |
| 2018/0110714 A1 | 4/2018 | Glenn, Jr. |
| 2018/0235861 A1 | 8/2018 | Smyth |
| 2018/0235862 A1 | 8/2018 | Smyth |
| 2020/0253850 A1 | 8/2020 | Smyth et al. |
| 2021/0128434 A1 | 5/2021 | Smith, III et al. |
| 2021/0169763 A1 | 6/2021 | Smith, III et al. |

FOREIGN PATENT DOCUMENTS

| | | |
|---|---|---|
| CA | 2631077 C | 3/2015 |
| CN | 1252263 A | 5/2000 |
| CN | 101193619 A | 6/2008 |
| CN | 103893060 A | 7/2014 |
| DE | 4315396 A1 | 11/1994 |
| DE | 19624051 A1 | 12/1997 |
| EP | 0232153 A2 | 8/1987 |
| EP | 0316726 A2 | 5/1989 |
| EP | 0368146 A2 | 5/1990 |
| EP | 0743310 A1 | 11/1996 |
| EP | 0780464 A2 | 6/1997 |
| EP | 1714678 A1 | 10/2006 |
| EP | 1859777 A2 | 11/2007 |
| EP | 2042216 B1 | 9/2015 |
| FR | 2998476 A1 | 5/2014 |
| GB | 2223236 A | 4/1990 |
| GB | 2280682 A | 2/1995 |
| GB | 2284215 A | 5/1995 |
| GB | 2351979 A | 1/2001 |
| GB | 2371307 A | 7/2002 |
| JP | 9194877 A | 7/1997 |
| JP | H1018177 A | 1/1998 |
| JP | 1053795 A | 2/1998 |
| JP | H1053795 A | 2/1998 |
| JP | 10182366 A | 7/1998 |
| JP | 2000212031 | 8/2000 |
| JP | 2001213762 A | 8/2001 |
| JP | 200445869 | 12/2004 |
| JP | 3644658 B2 | 5/2005 |
| JP | 2007320884 A | 12/2007 |
| JP | 2010138348 A | 6/2010 |
| JP | 2010150315 A | 7/2010 |
| JP | 2012001597 A | 1/2012 |
| JP | 4915720 B2 | 4/2012 |
| JP | 4965869 B2 | 7/2012 |
| JP | 5465872 B2 | 4/2014 |
| WO | WO9418946 A1 | 9/1994 |
| WO | 9616160 A1 | 5/1996 |
| WO | WO9612787 A1 | 5/1996 |
| WO | WO9730688 A1 | 8/1997 |
| WO | WO9748378 A1 | 12/1997 |
| WO | 9806817 A1 | 2/1998 |
| WO | WO200062755 A1 | 10/2000 |
| WO | WO0076460 A2 | 12/2000 |
| WO | WO0137658 A2 | 5/2001 |
| WO | WO0142409 A1 | 6/2001 |
| WO | WO02066589 A2 | 8/2002 |
| WO | WO02092050 A2 | 11/2002 |
| WO | WO02097020 A2 | 12/2002 |
| WO | 2004045576 A1 | 6/2004 |
| WO | WO2008110995 A2 | 9/2008 |
| WO | WO2010052070 A2 | 5/2010 |
| WO | WO2010052071 A2 | 5/2010 |
| WO | WO2010052147 A2 | 5/2010 |
| WO | WO2011049932 A1 | 4/2011 |
| WO | 2011094714 A1 | 8/2011 |
| WO | WO2012055855 A1 | 5/2012 |
| WO | WO2013007473 A2 | 1/2013 |
| WO | WO2013163074 A1 | 10/2013 |
| WO | WO2014090959 A1 | 6/2014 |
| WO | 2016026777 A1 | 2/2016 |
| WO | WO2016077114 A1 | 5/2016 |
| WO | WO2016149166 A1 | 9/2016 |
| WO | WO2016172405 A1 | 10/2016 |
| WO | WO2016172468 A1 | 10/2016 |
| WO | WO2016172472 A1 | 10/2016 |
| WO | WO2016172475 A1 | 10/2016 |
| WO | WO2016172478 A1 | 10/2016 |
| WO | WO2016172482 A1 | 10/2016 |

OTHER PUBLICATIONS

Dow—Methocel Cellulose Ethers Technical Handbook, p. 1-32, Jun. 1997.*

U.S. Appl. No. 15/435,533, filed Feb. 17, 2017, Kelsey Marie Smyth et al.

U.S. Appl. No. 15/435,546, filed Feb. 17, 2017, Kelsey Marie Smyth et al.

U.S. Appl. No. 15/299,692, filed Oct. 21, 2016, Edward Dewey Smith, III.

U.S. Appl. No. 15/787,832, filed Oct. 19, 2017, Edward Dewey Smith, III.

International Search Report and Written Opinion of the International Searching Authority, PCT/US2017/057555, dated Nov. 20, 2017, 13 pages.

All final and non-final office actions for U.S. Appl. No. 15/435,533 (P&G Case 14728).

All final and non-final office actions for U.S. Appl. No. 15/787,832 (P&G Case 14559M).

All final and non-final office actions for U.S. Appl. No. 16/862,666 (P&G Case 14729C).

All Office Actions, U.S. Appl. No. 15/135,627 (P&G Case No. 13805M).

All Office Actions, U.S. Appl. No. 15/135,648 (P&G Case No. 13806M).

(56) References Cited

OTHER PUBLICATIONS

All Office Actions, U.S. Appl. No. 15/135,659 (P&G Case No. 13807M).
All Office Actions, U.S. Appl. No. 15/135,675 (P&G Case No. 13808M).
All Office Actions, U.S. Appl. No. 15/135,687 (P&G Case No. 13815M).
All Office Actions, U.S. Appl. No. 15/135,697 (P&G Case No. 13816M).
International Search Report and Written Opinion of the International Searching Authority, PCT/US2016/028827, dated Jul. 28, 2016, 10 pages.
International Search Report and Written Opinion of the International Searching Authority, PCT/US2016/028832, dated Jun. 15, 2016, 10 pages.
International Search Report and Written Opinion of the International Searching Authority, PCT/US2016/028835, dated Jul. 27, 2016, 10 pages.
International Search Report and Written Opinion of the International Searching Authority, PCT/US2016/028840, dated Jul. 27, 2016, 10 pages.
International Search Report and Written Opinion of the International Searching Authority, PCT/US2016/028843, dated Jul. 27, 2016, 10 pages.
International Search Report and Written Opinion of the International Searching Authority, PCT/US2016/028846, dated Jul. 27, 2016, 10 pages.
International Search Report and Written Opinion of the International Searching Authority, PCT/US2017/057354, dated Jan. 5, 2018, 11 pages.
International Search Report and Written Opinion of the International Searching Authority, PCT/US2018/017738, dated May 9, 2018, 13 pages.
International Search Report and Written Opinion of the International Searching Authority, PCT/US2018/017741, dated May 9, 2018, 12 pages.
PCT International Search Report and Written Opinion for PCT/US2016/066752 dated Feb. 22, 2017.
U.S. Appl. No. 16/862,666, filed Apr. 30, 2020, Smyth et al.
All final and non-final office actions for U.S. Appl. No. 17/141,581.
All final and non-final office actions for U.S. Appl. No. 17/176,404.
All final and non-final office actions for U.S. Appl. No. 17/176,417.
All Office Actions, U.S. Appl. No. 15/435,546.
Oetter et al., Ringing Gels and their Fascinating Properties, Colloids and Surfaces, vol. 38, 1989, pp. 225-250.
PLUS Search generated internally by the US PTO support staff for this application attached and using STIC internal services, Feb. 24, 2021 (Year: 2021).
STIC Search Report generated by the US PTO support staff for this application (Chen Haoyi) attached, Feb. 25, 2021, 16 pages.

* cited by examiner

PERSONAL CLEANSING COMPOSITIONS AND METHODS

FIELD OF THE INVENTION

This application relates to rinse-off cleansing compositions with surfactant, perfume, structurant, solvent, and water; and methods relating thereto.

BACKGROUND OF THE INVENTION

Cleansing is an activity that has been done for hundreds of years. Early cleansers were based on either soap chemistry or simple mechanical action in order to remove dirt from the skin, as well as endogenous soils such as sweat, sebum and body odors. Smelling clean is an important benefit but early cleansers did not provide perfume to the skin during cleansing as it would have been wasteful for a very expensive ingredient, the perfume. Instead, perfume was applied after cleansing. As skin cleansing compositions have become more complex, providing scent during cleansing and residual scent on the skin after cleansing are expected by users of modern skin cleansers. As such, improved cleansing compositions which can provide scent during cleansing and/or residual scent on the skin are desired.

SUMMARY OF THE INVENTION

A rinse-off cleansing composition, comprising: a. from 11% to 17%, by weight of the composition, of a surfactant; b. from 1.4% to about 5%, by weight of the composition, of a perfume; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

A liquid rinse-off cleansing composition, comprising: a. from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume, wherein the weight percent of perfume is from about 10% to about 90%, by weight of the surfactant; c. from about 1.5% to about 8%, by weight of the composition, of a hydric solvent comprising dipropylene glycol, diethylene glycol, dibutylene glycol, pentanediol, heptanediol, or a combination thereof; d. from about 0.1% to about 4%, by weight of the composition, of a water soluble polymeric thickener; and e. from about 58% to about 93%, by weight of the composition, of water.

A liquid rinse-off personal cleansing composition, consisting essentially of: a. from about 5% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol; d. from about 0.5% to about 4%, by weight of the composition, of hydroxypropylmethyl cellulose; e. from about 58% to about 93%, by weight of the composition, of water; and f. optionally, one or more addition ingredients comprising a dye, pH modifier, a preservative, or a combination thereof.

These and other compositions will be more fully understood in light of the detailed description below.

DETAILED DESCRIPTION OF THE INVENTION

I. Definitions

As used herein, the following terms shall have the meaning specified thereafter:

"Cleansing composition" refers to compositions intended for topical application to the skin or hair for cleansing.

"Free of" refers to no detectable amount of the stated ingredient or thing.

"Hydric solvent" refers to a solvent that is neutral organic species that contains at least 2 hydroxyl groups and is not a hydrotrope.

"Hydrotrope" refers to a charged, amphiphilic solubility modifier. Hydrotropes are generally charged olefins especially an olefin sulfonate such as an aromatic sulfonate.

"Micelle" as used herein refers to a thermodynamically stable self-assembled structure comprising individual surfactant molecules aggregated to form a hydrophobic core region with externally facing polar head groups in equilibrium with surfactant monomers in a polar phase, having a characteristic dimension that is a single digit multiple of the surfactant length, i.e., generally less than about 10 nm in diameter.

"Microemulsion" as used herein refers to a thermodynamically stable isotropic mixture of oil, surfactant, and water comprising an interior hydrophobic core, having a size greater than about 10 nm diameter.

"Perfume" refers to a mixture of volatile organic oils having a pleasant aroma wherein the perfume components have individual molecular weights between about 75 and 400 Daltons.

"Rinse-off" means the intended product usage includes application to skin and/or hair followed by rinsing and/or wiping the product from the skin and/or hair within a few seconds to minutes of the application step. The product is generally applied and rinsed in the same usage event, for example, a shower.

"Room temperature" refers to a temperature of 25° C.

"Stable" when used herein with respect to inventive cleansing compositions refers to phase stability. The compositions should not separate into distinctly visible layers upon storage under ambient conditions for at least 1 mo.

"Substantially free of" refers to about 2% or less, about 1% or less, or about 0.1% or less of a stated ingredient.

"Surfactant" as used herein refers to synthetic amphiphilic molecules which can aggregate to form micelles and other surfactant structures.

II. Cleansing Compositions

Modern consumers of cleansing compositions expect the composition to provide scent both during use and to have residual scent on the skin after use, making perfume an important component of cleansing compositions. Perfume is also an important component of many skin cleansers to mask the base odor of cleansing ingredients, which can be unpleasant.

Perfume is hydrophobic, whereas skin cleansers generally have an aqueous, continuous phase which provides essentially no ability to carry perfume. It is desirable to provide perfume in a soluble form in a liquid skin cleanser, since insoluble phases of any kind can lead to instability problems in the composition. Perfume is therefore generally solubilized within the surfactant component of cleansers, such as micelles, lamellar structures, vesicles and the like. Surfactant structures of all kinds contain hydrophobic regions due to the aggregation of surfactant tails, which are able to solubilize perfume oil. Perfume generally exists within the surfactant tails as a molecular solution due to the interaction of the perfume with the surfactant tails, not as a colloidal structure such as an emulsion droplet, which is not thermodynamically stable.

A problem exists in providing perfume scent during use and residual scent to the skin from skin cleansers. Well known physical laws govern the relationship between perfume in the air in equilibrium with perfume solubilized in a micelle or other surfactant environment. This relationship is defined by the mole fraction of perfume in the soluble environment, e.g., the micelle. Micelles are common features of skin cleansers since even non-micellar surfactant generally become micelles during the dilution experienced while cleansing.

Since the perfume concentration in a skin cleanser is generally only 25% or less on a molar basis in the surfactant micelle, the vapor pressure of all the perfume molecules can be reduced by 75% or even more, due to its solubilization in the micelle. The desire to deliver perfume to the skin suffers from a similar fate during cleansing. Perfume molecules can "jump", or partition, into the skin during cleansing. The driving force to do so is the thermodynamic activity coefficient gradient for the perfume molecules. While a pure perfume applied to the skin, having an activity coefficient of 1, can partition quickly into skin, perfume located in a surfactant micelle proximal to the skin suffers from the activity coefficient reduction (75% or more) due to micellar solubilization. Therefore most perfume in cleansing compositions (between 50-90%) generally is washed away during rinsing before a significant amount can partition into the skin. The result is the skin retains no or very little scent and only for a short duration after a typical cleansing event. Thus, delivery of perfume to the air and to the skin during cleansing is inefficient and therefore expensive.

Overcoming these technical constraints in order to increase initial perfume perception in a neat composition, perfume delivery to the air during cleansing, and to the skin is not simply a matter of adjusting formula components at increased cost. Natural limits exist related to factors such as solubility. For example, increasing perfume in a composition is not only impractical from a cost standpoint, perfume being quite expensive, but is also infeasible considering the abundance of perfume can quickly become insoluble in the surfactant composition, leading to instability. Formulating a perfume to contain more, high vapor pressure components to enhance bloom may be useful, but does not overcome the innate vapor pressure reduction of perfume due to solubilization in the micelle, in addition to other restrictions to the scent character that would result. Benefits of these approaches are limited.

Various means to overcome this problem have been suggested. Perfume microcapsules have been developed to encapsulate perfume and protect it from contact with surfactant. However, only a limited number of perfume molecules are stable in perfume microcapsules; and the perfume microcapsule itself must then be delivered to the skin and, later, mechanically crushed by the consumer in order to release the perfume. Most perfume microcapsules are themselves washed down the drain during cleansing, affording little benefit.

Additionally, cleansing compositions have been formulated as micelles. Surfactants have a critical micelle concentration, or CMC, at which they aggregate. Below the CMC surfactant exists as monomers in solution. It has been suggested that dilution to below the CMC can release perfume to increase bloom. The problem with this approach is the CMC is very low, often about 100 ppm for cleansing surfactant mixtures (i.e., 0.01 wt. %, a dilution of more than 500-fold from the original composition). Thus, the CMC occurs at concentrations not relevant to cleansing nor rinsing the body. During rinsing, the CMC is reached only at the very end of cleansing, by which time nearly all the cleansing components have already been washed down the drain in the form of micelles, carrying the perfume with them. Relevant dilutions during cleansing are less than 10-fold, especially less than 5-fold, during which time there is extensive exposure of the wash composition to the body and to the air in the shower, affording both time and opportunity for perfume to bloom and partition to the skin, if it can be removed from the environment of the micelle.

A constraint in overcoming these problems relates to the rheology profile of the composition. Liquid skin cleansing compositions generally require dosing from a package onto a hand, a cleansing implement, or the skin itself without running off. Further, compositions should spread easily across the body to effect thorough cleansing. Historical means to provide an acceptable rheology involved the use of surfactants to form elongated micelles or lamellar structures without the use of other rheology control agents, which can be wasteful and costly. Control of rheology using surfactants, however, can provide important restrictions which limit the ability to modify surfactant mixtures to provide other benefits, such as perfume benefits.

Surprisingly, inventors have discovered skin cleansing compositions can deliver enhanced initial perfume perception, perfume bloom during cleansing, and perfume retention on the skin for many hours after cleansing. Without wishing to be limited by theory, the enhanced perfume benefits are believed to result at least in part when at least a portion of the perfume in a composition during its use as a cleanser exists in the physical form of a perfume microemulsion. In some cases, the microemulsion may be in equilibrium with other phases such as micelles or a lamellar phase. In some cases, the microemulsion can spontaneously form upon addition of water, i.e., during cleansing or rinsing. In the microemulsion form, it is believed most perfume is in the central core region and is not proximal to surfactant hydrocarbon, therefore it is not in a solvent-solute relationship which can reduce perfume activity coefficient. The result is bloom is significantly enhanced; and scent of perfume over the skin after wash, can also be enhanced. Further, kinetic effects may occur which are difficult to quantify by equilibrium measures, such that exposure of the composition to water during cleansing preferentially leaches hydrophilic components from the surfactant phase, such as low molecular weight hydric solvents and surfactants, leaving behind a composition enriched in less polar components. The result of these transient effects can be compositions that do not follow a predictable, thermodynamic (equilibrium) dilution path during use, but rather bifurcate during use to a generally polar and a less polar mixture. Furthermore, evaporation of the most volatile perfume components and skin adsorption of more hydrophobic perfume components steadily changes the chemical composition of the cleansing mixture during use.

To make a perfume microemulsion, sufficiency of perfume, which is the oil component for making a perfume core; the right level and mixture of surfactant; and a hydric solvent able to interact in a manner to make the microemulsion are believed to be contributing factors. The hydric solvent has multiple effects like, reducing the dielectric of the water phase, acting as a solvent for the surfactant head groups, and interacting with the perfume in the core. Hydric solvents can be chameleonic in nature, able to provide miscibility with hydrophobic perfume oil and water external to the microemulsion phase. During use of the body cleansing composition, as the composition is diluted, hydric solvent can be reduced in concentration in a perfume microemulsion core because of the abundance of water added during washing and rinsing, providing a further benefit to increase perfume activity coefficient by increasing perfume molar concentration in the core. Thus, a sufficient amount of particular kinds of hydric solvents can be used to form a microemulsion phase which can increase perfume activity during use.

For compositions with a lower surfactant concentration, like less than 19%, controlling the rheology so that it is still acceptable to be delivered from a bottle and still delivering a perfume benefit can be a challenge. Polymeric thickening agents can be used to control rheology, but there are limited polymers able to thicken mixtures with surfactant up to 19 wt % of the composition, having significant quantities of electrolyte accompanying surfactant or added separately, and having significant amounts of perfume. The polymer can also create new phase restrictions or constraints by interacting with micelles in ways that may minimize the beneficial aspects of the perfume microemulsion. Overcoming the problems related to perfume benefits in cleansing compositions while maintaining an acceptable rheology profile for dispensing is therefore a highly constrained problem and difficult to overcome. Control of rheology in compositions having a lower surfactant concentration can be particularly challenging in compositions which utilize solvents to enhance perfume delivery, because the relatively low levels of surfactant minimize their rheology contribution while at the same time the solvents also reduce rheology attributes such as viscosity and G' (elasticity).

Compositions with less than 19% surfactant tend not to form structured phases, i.e., they are typically not lamellar, with few exceptions that relate to use of surfactants with very specific packing parameter. This is increasingly true when hydric solvents are used, since hydric solvents essentially dissolve lamellar structures by their interaction with the surfactants, especially by solvation of the polar region of the surfactant molecules.

Inventors have found conventional means of thickening compositions having up to 19% surfactant, electrolyte added and accompanying the surfactant up to 2%, and hydric solvent up to about 2% or more, are difficult. Typically aqueous polymers such as xanthan gum and polyacrylate polymers provide minimal thickening because of the unique solvent environment of the composition. Similarly, physical gelling agents such as ethylene glycol distearate and trihydroxystearin provide little thickening because of a combination of the added surfactants they can contain and the unique solvent environment which changes the interaction potential of their crystal structures. Components like salt, fatty alcohol, and fatty acid, change the nature of the surfactant structure itself, so are not useful since the surfactant structure is designed to provide perfume delivery benefits. Surprisingly, inventors have found polymers which interact with the surfactant structures of the inventive compositions to form a gel without changing the nature of the surfactant structures. These polymers are nonionic and utilize surfactant structures in order to interact to form a network (gel).

Further, the gels formed in the current invention do not require all surfactant to participate, so that one portion provides a network to deliver a useful rheology profile, while another portion of surfactant can remain unstructured, which can be important to delivery of perfume benefits. The relative proportions of component phases of the composition can be evaluated microscopically or using an ultracentrifuge to separate them.

In order to show a benefit from formulating in this space, an inventive composition (Inventive Example 1—with different perfume) is tested versus a micellar body wash with 14% surfactant (Comparative Example 1). As illustrated in the tables below, Inventive Composition 1 shows a statistically better scent intensity through the time interval of 30 minutes after application through the time point of 4 hours after application and won on overall rating.

|  | Inventive Example 1 | Comparative Example 1 |
| --- | --- | --- |
| Intensity at 30 minutes | 3.1 a | 2.4 b |
| Intensity at 60 minutes | 2.4 a | 1.6 b |
| Intensity at 90 minutes | 1.9 b | 1.3 c |
| Intensity at 2 hours | 1.8 a | 1.3 b |
| Intensity at 4 hours | 1.4 a | 0.7 b |

*Values with different lower case letters are significantly different

|  | Inventive Composition 1 | Comparative Composition 1 |
| --- | --- | --- |
| Overall Rating | 68 | 57 |
| Long Lasting scent (4 hours) | 44 | 31 |

Some compositions may be in a lamellar phase prior to use, but can be transformed to a perfume microemulsion during aqueous dilution. In some cases, the transformation during dilution to a perfume microemulsion may be brief, within a restricted dilution range, but such range is sufficient to deliver perfume bloom and partitioning into the skin which, once partitioning is effected, it cannot be reversed. Certain microemulsions may be in equilibrium with other phases, such as micelles or a lamellar phase, either in the composition or during dilution of the composition during use. There may be advantages for both the microemulsion and micelle phases to coexist, since micelles may provide superior lather and cleaning properties at the same time the microemulsion may deliver enhanced perfume benefits. Certain analytical measures, such as dynamic light scattering, can be used as guides, when evaluating microemulsion phases. Additionally, perfume analysis in the headspace is directly relatable to the perfume solvent environment in a composition or a diluted composition, so that gas chromatography-mass spectrometry (GCMS) headspace measures are an indicator of the perfume environment, i.e., the microemulsion phase and the perfume relationship to solvent molecules therein. Well established physical laws govern the relationship between concentration of molecules in the headspace, and the solvent environment of the molecules in solution, e.g., Raoult's Law. Likewise, headspace measurements over the skin after washing are similarly useful, since perfume partitioning into the skin is enhanced by perfume activity coefficient, as previously discussed.

Dynamic Light Scattering is a useful means to detect structures in the size range of microemulsion droplets, and micelles, but the method can be influenced by artifacts especially when more than one structure may be present, such as micelles and a microemulsion both. A bimodal scattering intensity distribution may be present in inventive compositions, suggesting micelles having a diameter generally below 10 nm in equilibrium with larger structures, which are generally greater than about 20 nm which are the perfume microemulsion droplets.

A microemulsion phase generally has a low viscosity and is a Newtonian fluid. Cleansing fluids with these viscosity characteristics are generally useful when dispensed from a package which controls the dose or spreads it onto the target surface, such as a pump foamer or a spray. To fit with current consumer habits during body cleansing, a cleansing composition can be in the form of a gel having a structure defined by an elastic modulus, G', a viscous modulus, G", a viscosity, and a shear thinning viscosity ratio as measured by the test methods below. A microemulsion composition can be concentrated to create a gel, wherein the gel provides a suitable rheology to easily dispense the composition from a package, and wherein the gel may comprise a lamellar phase or at least a more structured phase of some kind. However, concentration extends the composition into higher surfactant concentrations than the current invention, such as for example 25% or 30% or 40% or more. Concentration thus requires new packaging and therefore higher costs, in addition to changes in habits of the user. A composition using an alternate means of providing structure that does not influence the microemulsion phase and therefore the perfume benefits is ideal but no such composition or means to structure it exists today, as described above.

Additionally, organic solvents are useful to help form a microemulsion phase. Some organic solvents are miscible in water, at least partially miscible in perfume oil, and can interact with surfactant polar head groups to reduce structure and generally reduce viscosity as a result. The microemulsion phase requires very low interfacial tension. Perfume can be essentially relegated to the core of a water continuous microemulsion phase and therefore has a high activity coefficient, which can be effected by using a hydric solvent having water, perfume oil, and surfactant miscibility to reduce interfacial tension.

Water miscibility of hydric solvent can be determined by mixing the solvent with water and measuring turbidity as an indicator of solubility. When mixtures are less than fully transparent, the mixture is no longer a molecular solution. Hydric solvents that are fully miscible with water at ambient temperature and shower temperature tend to work well in helping with microemulsion formation. A spectrophotometer can be used to measure miscibility by optical clarity, by measuring % light transmission at a visible wavelength of light such as 640 nm. Hydric solvent is added in increasing amounts to water, measuring optical clarity. When all mixtures are optically transparent, the solvent is fully water miscible. If some mixtures are less than transparent, the concentration of hydric solvent at the onset of turbidity is its aqueous solubility.

Perfume miscibility of a hydric solvent can be determined by mixing the solvent with a representative perfume or perfume molecule and measuring optical clarity. When the perfume-solvent mixture is less than fully transparent the mixture is no longer a molecular solution. Hydric solvent is added until past the point of optical clarity, using a spectrophotometer to measure % Transmission for the mixture at an optical wavelength. Perfume miscibility is defined as the highest percentage of hydric solvent that can be added to a perfume, based on the weight of the two, which remains optically clear, i.e., generally 100% T at 640 nm. Exemplary hydric solvents are at least about 10%, 15%, or 20 wt % miscible in the target perfume based on total weight of the perfume-solvent mixture. When solvent is miscible with both perfume and water, surface tension between the water and perfume phases in a composition can be lower, which creates optimal conditions for the formation of a microemulsion. When miscibility with both water and perfume is even higher, i.e., as high as 100%, solvent located in a microemulsion core with perfume can rapidly migrate to the aqueous phase during product use. The abundance of additional water during cleansing thus can reduce solvent in the microemulsion perfume core, reducing its action as a perfume solvent. This increases the thermodynamic activity coefficient of the perfume allowing it to both bloom in the shower and partition into the skin to provide superior scent longevity.

Perfume miscibility of a hydric solvent can vary by perfume since each perfume has unique chemical components. Perfume miscibility can be measured for a particular solvent in a specific perfume, such as the table below demonstrates for the perfume having the components listed below.

A perfume, perfume X, was used having these below in addition to other components, the components below were identified from the spectra, area counted and summed PRM (KI): Alpha pinene (940), camphene (955), myrcene (990), para-cymene (1028), d-limonene (1034), eucalyptol (1037), dihydromyrcenol (1071), alpha terpinene (1022), linalool (1107), camphor (1154), methyphenylcarbinyl acetate (1193), florol major 2 (1197), allyl amyl glycolate major (1234), linalyl acetate (1254), coranol (1275), 1H-Indene,2,3-dihydro-1,1,2,3,3-pentamethyl (1325), neryl acetate (1364), cyclemax (1427), coumarin (1449), gamma methyl ionone (1491), butylated hydroxyl toluene (1519), cashmeran (1517), methyldihydrojasmonate (1663), cis-hexenyl salicylate (1680), Iso-E Super Major (1686), Helvetolide major (1727), ambroxan major 2 (1791), galaxolide (1874).

|  | Perfume x miscibility (% of solvent added) |
|---|---|
| dipropylene glycol | 100% |
| hexylene glycol | 100% |
| *PEG 300 | 57% |
| propylene glycol | 38.5% |
| 1,3-butanediol | 33.0% |
| 1,6-hexanediol | 25.1% |
| glycerin | 3.2% |

*Dow Chemicals Carbowax Sentry PEG 300 average molecular weight

Surfactant miscibility of a hydric solvent can also be important to ability of the microemulsion to form. Preferred hydric solvents can form an optically transparent mixture when 45 parts surfactant are mixed with 30 parts hydric solvent and 25 parts water, which mixture can absorb an additional 30 parts of perfume oil while remaining optically clear.

When a hydric solvent meets these aforementioned criteria, generally a transparent microemulsion can be formed in the presence of perfume and surfactant with the solvent such that the composition can absorb at least its own weight of perfume oil while retaining optical clarity. Generally, a micelle is only capable of absorbing about 25% perfume oil by weight of the surfactant. Whereas microemulsion compositions can absorb about 100% or more, of the weight of the surfactant, in perfume oil while retaining optical clarity. In some cases, it may take a day for the microemulsion to spontaneously form at ambient temperature.

One class of a hydric solvent that is miscible with water and many perfumes is glycol. Glycols may have a mixture of isomers. One exemplary glycol class is diols where the alcohol groups are separated by no more than 2 carbons on average. Suitable glycols can include, for example, dipropylene glycol, propylene glycol, butylene glycol, pentylene glycol, hexylene glycol, or combinations thereof. Glycols can include pure materials and mixtures of isomers. For example, hexylene glycol includes 1,6-hexane diol; 1,4-hexane diol; or methyl pentanediol structures having 2 alcohol groups, etc.

Hydric solvents can modify the rheological properties of the composition, particularly reducing the viscosity. It was previously discussed that concentrating a composition into a gel is one way to combat low viscosity. These types of compositions often exhibit a classic x-ray diffraction pattern of a lamellar phase. However, when the level of hydric solvent is greater than about 40%, by weight of the surfactant, it can be difficult to form a structured gel and thus the composition can have a much lower viscosity and is difficult to dispense from conventional body wash packages. When compositions with an exemplary rheology profile are desired, an intermediate level of hydric solvent can be used to deliver both exemplary rheology and perfume delivery properties. Thus, the hydric solvent can be from about 10% to about 40%, from about 12% to about 40%, from about 15% to about 35%, from about 17% to about 35%, from about 20% to about 30%, expressed as a weight percent of the surfactant.

Perfume is a benefit agent. Perfume benefits can be realized at different time points for cleansing compositions. Perfume in the package headspace can be important to select a product at the time of purchase. Perfume scent during cleansing, upon introduction of modest amounts of water, such as for example about 3 parts of water per part composition (i.e., a 3:1 dilution ratio), provides a benefit during skin cleansing. During skin cleansing, some perfume can partition into the outer layers of the skin or hair, which can provide a scented skin or hair benefit for a period of time after cleansing, called scent longevity. A governing property for both scent bloom and longevity is the activity coefficient of the perfume molecules, which is a thermodynamic term. Perfume molecules exhibit their vapor pressure only when they are pure. Diluted perfume molecules, whether diluted by surfactant in a micelle, organic solvent, water, etc., exhibit less than their pure vapor pressure. The amount of perfume in a headspace over a composition, diluted composition, or over the skin or hair can be measured analytically, as described in the methods section below. Benefits in initial fragrance intensity, bloom, or longevity can be demonstrated by comparing performance of the compositions before, during, and, or after a skin or hair cleansing event, compared to conventional body wash or shampoo compositions.

In addition to being a benefit agent, perfume is an oil and therefore can be a direct contributor to formation of phases responsible for its activity coefficient (as noted above), and therefore to scent bloom and longevity benefits. As discussed above, perfume oil can be added into micelle surfactant mixtures only to about 0.25 weight fraction of the surfactant before it phase separates, whereas cleansing compositions described herein can hold an equivalent weight of perfume relative to surfactant, or even more, while remaining transparent, including water diluted compositions.

Perfume can be a carrier for non-scented, hydrophobic additives. Additives which are at least 5 wt %, or at least 10 wt %, or at least 20 wt % miscible with perfume may be employed to increase delivery of the additives to the skin or hair. Any additive which provides a benefit to the skin or hair or the skin environment (e.g., the skin microbiome) may be employed. The additive may provide a direct or indirect benefit, such as antibacterial, antihyperproliferative, anti-inflammatory, chelation, pH regulation, antifungal, antiviral, control of disorders such as acne, atopic dermatitis, eczema, dermatitis, dandruff, antiaging, antiwrinkle, age spot reduction, sunscreen, hydration, moisturization, or any other skin benefit. An advantage of the present compositions is enhanced additive delivery to the skin or hair during cleansing. A further benefit is reduction in activity coefficient of the additive by dilution with perfume is transient due to subsequent evaporation of the perfume on the skin, which increases the thermodynamic activity of the additive after its delivery to the skin.

A cleansing composition can also include a thickener. The thickener can help to control the rheology difficulties that arise from having a lower surfactant level and utilization of solvent to help with microemulsion formation.

In accordance with the above, a cleansing composition comprises a surfactant, a hydric solvent, perfume, a thickener, and water. Additionally, optional ingredients may also be included as noted herein, for example, preservatives, pH modifiers, hydrophobic oils, additives, preservatives, soap, etc.

A. Surfactant

A rinse-off cleansing composition includes surfactant. Surfactants can provide a cleaning benefit, lather properties, and rheology properties to the compositions. The surfactant may be a single surfactant or a combination of multiple surfactants. In addition, a surfactant may be branched, linear, or a combination thereof. A composition may comprise from 11% to about 17%, from 11% to about 16%, from 11% to about 15%, or from 11% to about 14%, by weight of the composition, of surfactant. The previous weight percentages of surfactant in the composition include primary surfactant and any cosurfactant.

The primary surfactant may be anionic. The rinse-off cleansing composition may include from about 5% to about 17%, from about 6% to about 17%, from about 7% to about 16%, from about 8% to about 16%, or from about 6% to about 14%, by weight of the composition, of an anionic surfactant.

The anionic surfactant can contain any counter ion such as sodium, potassium, ammonium, triethanolamine, etc. The hydrocarbon chain can be an olefin or be branched or linear or cyclic, such as alkyl benzenes, and generally has between 10 and 20 carbons or 12 to 16 carbons. The anionic surfactant can comprise ethylene oxide groups, such as one EO, or two EO, or three EO, e.g., and can be a sulfate, sulfonate or carboxylate, including acidic sulfonates such as sulfosuccinates.

Suitable anionic surfactants can include, for example, sodium trideceth sulfate and sodium laureth sulfate. These materials can have varying levels of ethoxylation. Thus, the levels of ethoxylation are represented by an (n), for example, sodium trideceth-n sulfate. n can range from about 0.5 to about 5. Some exemplary anionic surfactants are sodium trideceth-2 sulfate, sodium trideceth-3 sulfate, sodium laureth-1 sulfate, sodium laureth-2 sulfate, sodium laureth-3 sulfate, or combinations thereof.

The rinse-off cleansing composition may include from about 1% to about 15%, from about 2% to about 10%, about 2% to about 7%, or from about 4% to about 8%, by weight of the composition, of cosurfactant. The cosurfactant may be, for example, zwitterionic surfactant, amphoteric surfactant, nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the rinse-off cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the rinse-off cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl amidopropyl betaine, like cocoamidopropyl betaine.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocoamide monoethanolamine, decyl glucoside, or a combination thereof.

B. Perfume

A rinse-off cleansing composition includes a perfume. A composition may comprise from about 1.4% to about 5%, from about 1.5% to about 4.5%, from about 2.0% to about 4%, by weight of the composition, of perfume.

Perfume may be mixed with solvents such as triethyl citrate, isopropyl myristate, dipropylene glycol, or others, to help, for example, with the miscibility of the perfume molecules with each other or to reduce cost. Generally these perfume solvents provide minimal or negligible effects on surfactant compositions as a whole due to the low amount of perfume in the total composition and the amount of solvent in a perfume can be ignored. However, when solvent in the perfume accounts for more than about 5 wt % of the total hydric solvent in the cleansing composition, it must be accounted for. For example, when a perfume that is 10% hydric solvent is added to a cleansing composition at a level of 10 wt. % and the composition has 10 wt. % of added hydric solvent, the 1 wt. % of hydric solvent from the perfume accounts for a 9% bump in hydric solvent in the cleansing composition (1/11). Since this is more than a 5% change in the hydric solvent in the composition, it is accounted for. In this case, hydric solvent from the perfume is added (mathematically) to the hydric solvent from other sources added to the composition; and perfume is considered to comprise only the scented molecules and not the solvent, which is subtracted from the wt % perfume in the composition.

In addition, the weight ratio of perfume to surfactant can impact the ability of the composition to provide an enhanced fragrance benefit. Without being limited by theory, it is believed at least some of the perfume benefits, like bloom and residual scent are derived from an abundance of perfume on the basis of its relation to the surfactant due at least in part to the interaction of the perfume with surfactant as the composition is diluted. Perfume is soluble in surfactant micelles only to about 25% by weight of the surfactant. Above this level, the composition can become unstable unless steps are taken to form a phase to accept the abundance of perfume. However, forming those phases for stability of the perfume circles the composition back to where the perfume is bound within the composition and difficult to release. As such, a rinse-off cleansing composition comprises from about 10% 12%, 15%, 20%, 25%, 30%, 35%, 40%, to about 30%, 40%, 50%, by weight of the surfactant, of perfume.

Perfumes generally contain a broad range of perfume molecules (PRM) having diverse properties. It is an oversimplification to suggest all of the perfume is in a particular location, like in the core of a microemulsion. The real picture is more complex, with perfume molecules in dynamic equilibrium and structures such as micelles and microemulsions can be percolating. Further, some perfume molecules may favor being among surfactant tails or even in the aqueous phase instead of the microemulsion core. In short, all perfume molecules within a perfume mixture do not behave identically. Certain generalizations are useful to explain observed behaviors without inferring that all molecules in a perfume behave identically. For our purposes, a broad array of perfume molecules in a perfume mixture is analyzed by averaging or summing their performance.

Certain perfume features may also impact perfume benefits, such as the proportion of perfume molecules within a volatility or molecular weight range. In general, Kovats Index (KI) is a useful parameter to differentiate perfume molecules. Perfume molecules having KI less than 1100 can be considered high blooming molecules; those having KI greater than 1400 can be considered high skin partitioning molecules; and those between (KI of 1100-1400) can be considered middle perfume notes which generally favor neither bloom nor skin partitioning, but contribute to some extent in both.

Perfume can be tailored to enhance features of the compositions. For example, while the compositions, including diluted compositions during use, can have a high activity coefficient, perfume molecules may selectively evaporate to enhance bloom or partition into the skin depending on their individual vapor pressure. It has surprisingly been discovered that the weight percentage of middle notes can impact the fragrance expression of the composition for the initial scent, for bloom and delivery on the skin. Particularly, better expression of the perfume is accomplished when the weight percentage of middle notes is restricted. For example, the composition may comprise a perfume, wherein the weight percentage of middle notes of the perfume comprises from about 0% to about 50%, from about 5% to about 30%, from about 5% to about 20%, or from about 5% to about 10%, by weight of the perfume.

C. Solvent

A rinse-off cleansing composition includes a solvent. A rinse-off cleansing composition may comprise from about 1% to about 10%, from about 1% to about 8%, from about 1.5% to about 8%, from about 1% to about 7%, from about 2% to about 7%, or from about 2% to about 6%, by weight of the composition, of the solvent.

The solvent can be a hydric solvent. The hydric solvent can be a glycol. Examples of acceptable hydric solvents include dipropylene glycol (a glycol ether), diethylene glycol, dibutylene glycol, hexylene glycol, butylene glycol, pentanediol, heptanediol, propylene glycol, a polyethylene glycol having an average molecular weight below about 500, or a combination thereof. One example of a polyethylene glycol is PEG 300. Isomers are included in the generally descriptive solvents listed, for example, butylene glycol is meant to include 1,2-butanediol and 1,3-butanediol and 1,4-butanediol. When solvents are solid in the pure form (e.g., 1,6-hexanediol), they are melted during the making process in which case they are also effective hydric solvents.

A cleansing composition may comprise from about 8%, 10%, 12%, 14%, 16%, 17%, 20%, 25%, 30%, 40%, 50%, or 60%, to about 40%, 50%, 60%, 70%, 80%, 90%, or 100%, or any combination thereof, by weight of the surfactant, of hydric solvent.

A solvent may also comprise a non-hydric solvent. Examples of non-hydric solvents include propylene carbonate, propylene glycol ethers, butyl butanoate, propyl propanoate, isopropyl propanoate, or a combination thereof. One example of a propylene glycol ether is propylene glycol monomethylether. The non-hydric solvent may comprise less than about 25%, 20%, 15%, 10% or 5% by weight of the solvent.

D. Water

A rinse-off cleansing composition includes water. Water may come in with other components or may be added as free water. A rinse-off cleansing composition may comprise from about 10% to about 80%, from about 20% to about 70%, from about 30% to about 70%, from about 40% to about 70%, or from about 50% to about 70%, by weight of the composition, of water.

In addition, the total weight percent of water and solvent can be important in the composition since this defines the amount of solvent phase in which the microemulsion or surfactant structures are distributed. The total amount of solvent phase (approximately, the additive inverse generally of the surfactant level) is a key driver of surfactant phases due to proximity of surfactants. Thus, the composition may comprise from about 13% to about 93%, from about 20% to about 90%, from about 30% to about 85%, from about 40% to about 75%, by weight of the composition, of the combination of water and solvent.

E. Thickener

A rinse-off cleansing composition includes a thickener. A thickener may be included in an amount of about 0.5% to about 6%, from about 0.5% to about 5%, from about 0.5% to about 4%, or from about 1% to about 3%, by weight of the composition. The thickener may be, for example a water soluble nonionic polymer.

Nonionic polymers can include, for example, cellulosic polymers. For cellulosic polymers, the polymer may be a cellulose ether. For example, a thickener can include hydroxypropyl methyl cellulose. Hydroxypropyl methylcellulose can come in a variety of viscosities from, for example, 3,500-5,500 cP (like DOW METHOCEL 40-0202); 60,000-90,000 cP (like DOW METHOCEL 40-0101); and 10,000-16,500 cP (like DOW METHOCEL 40-0100). Information on the viscosities of these materials, etc. can be found on DOW's website www.dow.com.

Some thickeners may be used in combination with higher viscosity hydroxypropyl methyl cellulose (3,500-5,000 cP range). These can include lower viscosity hydroxypropyl methyl cellulose with a viscosity of 2,600-5,000 cP (like DOW METHOCEL E4M PRM).

F. Rheology—Viscoelasticity and Viscosity

The rheological properties of rinse-off cleansing compositions can be characterized by viscoelastic parameters and a viscosity. The rheology of a composition can be defined by its $G'$ and $G''$ values, relating to the composition's structure. $G'$ and $G''$ are measured in accordance with the rheological properties method discussed herein. $G'$ and $G''$ describe a cleansing compositions elastic and viscous response to applied stress, characterizing how the material acts when dispensed from a bottle, sitting on the consumers implement or hand, and how a product spreads on application. It also impacts a consumer's perception of the product, for instance products with low $G'$ values flow too readily in use and are associated in consumer perception and can be perceived as dilute, personal cleansing products. The cleansing composition may have a $G'$ at about 1 Hz of about 25 Pa to about 3000 Pa; from about 50 Pa to about 2500 Pa, from about 100 Pa to about 1500 Pa, or from about 150 Pa to about 1000 Pa. The cleansing composition may have a $G''$ at about 1 Hz of about 20 Pa to about 250 Pa; from about 35 Pa to 200 about Pa, from about 40 Pa to about 150 Pa, or from about 50 Pa to about 100 Pa.

In addition, the cleansing composition should have a viscosity sufficient to allow it to be dispensed from a package onto an implement or directly onto the skin. The viscosity of a rinse-off cleansing composition is measured in accordance with the rheological properties method discussed herein. The cleansing composition may have a viscosity at about 0.10 l/sec of about 10 PaS to about 1200 PaS; from about 20 PaS to about 1000 PaS, from about 20 PaS to about 500 PaS, or from about 20 PaS to about 300 PaS. The cleansing composition may have a viscosity at about 10 l/sec of about 1 PaS to about 30 PaS; from about 1 PaS to about 20 PaS, from about 1 PaS to about 15 PaS, or from about 1 PaS to about 10 PaS.

Compositions can also be highly shear thinning, having a viscosity ratio of less than about 0.20, or 0.10, or even less than 0.05, which is the ratio of the viscosity at 1 l/sec divided by the viscosity at 0.10 l/sec.

G. Hydrophobic Oils

The rinse-off cleansing composition may comprise a hydrophobic oil. Hydrophobic oil can help form a microemulsion phase due to low solubility in the palisade layer of micelles, to further enhance bloom and deposition on skin. The rinse-off cleansing composition may comprise from about 0% to about 25%, from about 2% to about 20%, or from about 3% to about 15% by weight of the composition, of a hydrophobic oil. Exemplary hydrophobic oils can include, for example, isopropyl myristate, isostearyl isostearate, behenyl behenate, triglycerides such as soybean oil, hydrocarbon such as mineral oil, or combinations thereof.

H. Additives

The rinse-off cleansing composition may comprise an additive. Additives are materials that are at least partially soluble in the perfume. It is believed that additives which are at least partially soluble in the perfume will also see a deposition benefit. Additives which are at least 5 wt %, or at least 10 wt %, or at least 20 wt % miscible with perfume may be employed to increase delivery of the additives to the skin or hair. Some examples of classes of material that can be soluble in the perfume are skin actives, vitamins, antibacterials, antifungals, chelants, or combinations thereof.

Examples of skin actives which can be included are sunscreens; anti-acne medicaments; antioxidants; skin soothing agents, skin healing agents; essential oils, skin sensates, anti-wrinkle medicaments, or mixtures thereof. Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The rinse-off cleansing composition may comprise from about 1% to about 20%, from about 2% to about 10%, or from about 3% to about 8%, by weight of the composition, of an additive.

I. Soap

Rinse-off cleansing compositions as described herein may also comprise soap, for example, sodium myristate.

J. Methods

In addition to the compositional elements and parameters noted above, it is believed there are also some inventive benefits and/or uses to the compositions which are set out as methods below. For the sake of brevity, all of the compositional elements and parameters noted above are not repeated herein, but can be used within the methods where relevant.

A method of enhancing fragrance of a rinse-off cleansing composition before use, comprising, combining: a. from about 7% to 17%, by weight of the composition, of a surfactant; b. from 1.4% to about 5%, by weight of the composition, of a perfume, wherein the perfume is at least 20% of the weight of the surfactant; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

A method of enhancing fragrance of a rinse-off cleansing composition before use, comprising, combining: a. from about 5% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume, wherein the weight percent of perfume is from about 10% to about 90%, by weight of the surfactant; c. from about 1.5% to about 8%, by weight of the composition, of a hydric solvent comprising dipropylene glycol, diethylene glycol, dibutylene glycol, pentanediol, heptanediol, or a combination thereof; d. from about 0.1% to about 4%, by weight of the composition, of a water soluble polymeric thickener; and e. from about 58% to about 93%, by weight of the composition, of water.

A method of enhancing fragrance of a rinse-off cleansing composition before use, comprising, combining: a. from about 5% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol; d. from about 0.5% to about 4%, by weight of the composition, of hydroxypropylmethyl cellulose; and e. from about 58% to about 93%, by weight of the composition, of water.

A method of enhancing in-vitro bloom of a rinse-off composition, comprising, combining: a. from 11% to 17%, by weight of the composition, of a surfactant; b. from 1.4% to about 5%, by weight of the composition, of a perfume, wherein the perfume is at least 20% of the weight of the surfactant; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

A method of enhancing in-vitro bloom of a rinse-off composition, comprising, combining: a. from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume, wherein the weight percent of perfume is from about 10% to about 90%, by weight of the surfactant; c. from about 1.5% to about 8%, by weight of the composition, of a hydric solvent comprising dipropylene glycol, diethylene glycol, dibutylene glycol, pentanediol, heptanediol, or a combination thereof; d. from about 0.1% to about 4%, by weight of the composition, of a water soluble polymeric thickener; and e. from about 58% to about 93%, by weight of the composition, of water.

A method of enhancing in-vitro bloom of a rinse-off composition, comprising, combining: a. from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol; d. from about 0.5% to about 4%, by weight of the composition, of hydroxypropylmethyl cellulose; and e. from about 58% to about 93%, by weight of the composition, of water.

A method of enhancing fragrance of a rinse-off cleansing composition on skin or hair, comprising, combining: a. from 11% to 17%, by weight of the composition, of a surfactant; b. from 1.4% to about 5%, by weight of the composition, of a perfume, wherein the perfume is at least 20% of the weight of the surfactant; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

A method of enhancing fragrance of a rinse-off cleansing composition on skin or hair, comprising, combining: a. from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume, wherein the weight percent of perfume is from about 10% to about 90%, by weight of the surfactant; c. from about 1.5% to about 8%, by weight of the composition, of a hydric solvent comprising dipropylene glycol, diethylene glycol, dibutylene glycol, pentanediol, heptanediol, or a combination thereof; d. from about 0.1% to about 4%, by weight of the composition, of a water soluble polymeric thickener; and e. from about 58% to about 93%, by weight of the composition, of water.

A method of enhancing fragrance of a rinse-off cleansing composition on skin or hair, comprising, combining: from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol; d. from about 0.5% to about 4%, by weight of the composition, of hydroxypropylmethyl cellulose; and e. from about 58% to about 93%, by weight of the composition, of water.

A method of enhancing fragrance longevity of a rinse-off cleansing composition on skin or hair, comprising, combining: a. from 11% to 17%, by weight of the composition, of a surfactant; b. from 1.4% to about 5%, by weight of the composition, of a perfume, wherein the perfume is at least 20% of the weight of the surfactant; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

A method of enhancing fragrance longevity of a rinse-off cleansing composition on skin or hair, comprising, combining: a. from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol, diethylene glycol, dibutylene glycol, pentanediol, heptanediol, or a combination thereof; d. from about 0.1% to about 4%, by weight of the composition, of a water soluble polymeric thickener; and e. from about 58% to about 93%, by weight of the composition, of water.

A method of enhancing fragrance longevity of a rinse-off cleansing composition on skin or hair, comprising, combining: from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b. from about 1.5% to about 5%, by weight of the composition, of a perfume; c. from about 1.5% to about 8%, by weight of the composition, of a hydric solvent comprising dipropylene glycol; d. from about 0.5% to about 4%, by weight of the composition, of hydroxypropylmethyl cellulose; and e. from about 58% to about 93%, by weight of the composition, of water.

K. Exemplary Combinations

In this section, each paragraph further builds on the ones before it unless specifically limited.

A. A rinse-off cleansing composition, comprising: a. from 11% to 17%, by weight of the composition, of a surfactant; b. from 1.4% to about 5%, by weight of the composition, of a perfume; c. from about 1% to about 10%, by weight of the composition, of a hydric solvent, wherein the weight percent of the hydric solvent is from about 8% to about 60%, by weight of the surfactant; d. from about 0.5% to about 6%, by weight of the composition, of a thickener, and e. from about 58% to about 93%, by weight of the composition, of water; wherein the rinse-off cleansing composition has a G' at 1 Hz of about 25 Pa to about 3000 Pa.

B. The composition of paragraph A, wherein the composition comprises from 11% to about 17%, from 11% to about 16%, from 11% to about 15%, or from 11% to about 14% by weight of the composition, of surfactant.

C. The composition of paragraphs A and B, wherein the surfactant comprises a first anionic surfactant.

D. The composition of paragraph C, wherein the first anionic surfactant is branched.

E. The composition of paragraph C, wherein the first anionic surfactant comprises a sulfate, an alkyl ether sulfate, a sulfonate, a carboxylate, a sarcosinate, or a combination thereof.

F. The composition of paragraph C, wherein the first anionic surfactant comprises sodium trideceth-2 sulfate, sodium trideceth-3 sulfate, sodium laureth-1 sulfate, sodium laureth-2 sulfate, sodium laureth-3 sulfate, sodium cocoyl isethionate, or a combination thereof.

G. The composition of any of paragraphs A-F, wherein the surfactant further comprises from about 1% to about 15%, from about 2% to about 10%, about 2% to about 7%, or from about 4% to about 8%, by weight of the composition, of cosurfactant.

H. The composition of paragraph G, wherein the cosurfactant comprises a betaine.

I. The composition of paragraph G, wherein the cosurfactant comprises cocamidopropyl betaine.

J. The composition of any of paragraphs A-I, wherein the composition comprises from about 1% to about 8%, from about 1.5% to about 8%, from about 1% to about 7%, from about 2% to about 7%, or from about 2% to about 6%, by weight of the composition, of the solvent.

K. The composition of any of paragraphs A-J, wherein the hydric solvent comprises dipropylene glycol, diethylene glycol, dibutylene glycol, hexylene glycol, butylene glycol, pentanediol, heptanediol, propylene glycol, a polyethylene glycol having a weight average molecular weight below about 500, or a combination thereof.

L. The composition of any of paragraphs A-J, wherein the hydric solvent comprises dipropylene glycol, diethylene glycol, dibutylene glycol, hexylene glycol, butylene glycol, pentanediol, heptanediol, propylene glycol, a polyethylene glycol having a weight average molecular weight below about 500, or a combination thereof.

M. The composition of any of paragraphs A-J, wherein the solvent comprises dipropylene glycol.

N. The composition of any of paragraphs A-M, wherein the composition comprises from about 0.5% to about 5%, from about 0.5% to about 4%, or from about 1% to about 3%, by weight of the composition, of the thickener.

O. The composition of any of paragraphs A-N, wherein the thickener comprises hydroxypropylmethyl cellulose.

P. The composition of paragraph 0, wherein the hydroxypropylmethyl cellulose has a viscosity range of about 2,600 to about 90,000 cP.

Q. The composition of any of paragraphs A-P, wherein the composition has a G' at 1 Hz of about 50 Pa to about 2500 Pa, from about 100 Pa to about 1500 Pa, or from about 150 Pa to about 1000 Pa.

R. The composition of any of paragraphs A-Q, wherein the composition has a G" at 1 Hz of about 20 Pa to about 250 Pa, from about 35 Pa to about 200 Pa, from about 40 Pa to about 150 Pa; or from about 50 Pa to about 100 Pa.

S. The composition of any of paragraphs A-R, wherein the composition has a viscosity at a shear rate of 0.10 1/sec of about 10 PaS to about 1200 PaS; from about 20 PaS to about 1000 PaS, from about 20 PaS to about 500 PaS, or from about 20 PaS to about 300 PaS, when measured in accordance with the Viscosity Method; and/or a viscosity at a shear rate of 10 1/sec of about 1 PaS to about 30 PaS, from about 1 PaS to about 20 PaS, from about 1 PaS to about 15 PaS, or from about 1 PaS to about 10 PaS, when measured in accordance with the Viscosity Method.

T. The composition of any of paragraphs A-S, wherein the composition is a microemulsion or contains a microemulsion.

U. The composition of any of paragraphs A-T, wherein the composition is not in the form of a ringing gel.

V. The composition of any of paragraphs A-U, wherein at least a portion of the composition becomes a microemulsion upon dilution with water of about 3:1 by weight (water:composition) to about 10:1 by weight (water:composition).

W. The composition of any of paragraphs A-V, wherein the perfume is at least 20% of the weight of the surfactant.

X. Use of a rinse-off cleansing composition in any of claims A-W for enhancing fragrance of a rinse-off cleansing composition before use.

Y. Use of a rinse-off cleansing composition in any of claims A-W for enhancing in-vitro bloom of a rinse-off composition.

Z. Use of a rinse-off cleansing composition in any of claims A-W for enhancing fragrance of a rinse-off cleansing composition on skin or hair.

AA. Use of a rinse-off cleansing composition of any of claims A-W for enhancing fragrance longevity of a rinse-off cleansing composition on skin or hair.

BB. A liquid rinse-off cleansing composition, comprising: a) from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b) from about 1.5% to about 5%, by weight of the composition, of a perfume, wherein the weight percent of perfume is from about 10% to about 90%, by weight of the surfactant; c) from about 1.5% to about 8%, by weight of the composition, of a hydric solvent comprising dipropylene glycol, diethylene glycol, dibutylene glycol, pentanediol, heptanediol, or a combination thereof; d) from about 0.1% to about 4%, by weight of the composition, of a water soluble polymeric thickener; and e) from about 58% to about 93%, by weight of the composition, of water.

CC. The composition of paragraph BB, wherein the anionic surfactant comprises a sulfate, an alkyl ether sulfate, a sulfonate, a carboxylate, a sarcosinate, or a combination thereof.

DD. The composition of paragraph CC, wherein the first anionic surfactant comprises sodium trideceth-2 sulfate, sodium trideceth-3 sulfate, sodium laureth-1 sulfate, sodium laureth-2 sulfate, sodium laureth-3 sulfate, sodium cocoyl isethionate, or a combination thereof.

EE. The composition of any of paragraphs BB-CC, wherein the surfactant comprises from about 2% to about 7%, or from about 4% to about 8%, by weight of the composition, of the cosurfactant.

FF. The composition of any of paragraphs BB-EE, wherein the cosurfactant comprises a betaine.

GG. The composition of any of paragraphs BB-FF, wherein the cosurfactant comprises cocamidopropyl betaine.

HH. The composition of any of paragraphs BB-GG, wherein the composition comprises from about 1% to about 7%, from about 2% to about 7%, or from about 2% to about 6%, by weight of the composition, of the solvent.

II. The composition of any of paragraphs BB-HH, wherein the hydric solvent comprises dipropylene glycol, diethylene glycol, dibutylene glycol, hexylene glycol, butylene glycol, pentanediol, heptanediol, propylene glycol, a polyethylene glycol having a weight average molecular weight below about 500, or a combination thereof.

JJ. The composition of any of paragraphs BB-HH, wherein the hydric solvent comprises dipropylene glycol, diethylene glycol, dibutylene glycol, hexylene glycol, butylene glycol, pentanediol, heptanediol, propylene glycol, a polyethylene glycol having a weight average molecular weight below about 500, or a combination thereof.

KK. The composition of any of paragraphs BB-HH, wherein the solvent comprises dipropylene glycol.

LL. The composition of any of paragraphs BB-KK wherein the composition comprises from about 0.5% to about 4%, or from about 1% to about 3%, by weight of the composition, of the thickener.

MM. The composition of any of paragraphs BB-LL, wherein the thickener comprises hydroxypropylmethyl cellulose.

NN. The composition of paragraph MM, wherein the hydroxypropylmethyl cellulose has a viscosity range of about 2,600 to about 90,000 cP.

OO. The composition of any of paragraphs BB-NN, wherein the composition has a G' at 1 Hz of about 50 Pa to about 2500 Pa, from about 100 Pa to about 1500 Pa, or from about 150 Pa to about 1000 Pa.

PP. The composition of any of paragraphs BB-OO, wherein the composition has a G" at 1 Hz of about 20 Pa to about 250 Pa, from about 35 Pa to about 200 Pa, from about 40 Pa to about 150 Pa; or from about 50 Pa to about 100 Pa.

QQ. The composition of any of paragraphs BB-PP, wherein the composition has a viscosity at a shear rate of 0.10 l/sec of about 10 PaS to about 1200 PaS; from about 20 PaS to about 1000 PaS, from about 20 PaS to about 500 PaS, or from about 20 PaS to about 300 PaS, when measured in accordance with the Viscosity Method; and/or a viscosity a shear rate of 10 l/sec of about 1 PaS to about 30 PaS, from about 1 PaS to about 20 PaS, from about 1 PaS to about 15 PaS, or from about 1 PaS to about 10 PaS, when measured in accordance with the Viscosity Method.

RR. The composition of any of paragraphs BB-QQ, wherein the composition is a microemulsion or contains a microemulsion.

SS. The composition of any of paragraphs BB-RR, wherein the composition is not in the form of a ringing gel.

TT. The composition of any of paragraphs BB-SS, wherein at least a portion of the composition becomes a microemulsion upon dilution with water of about 3:1 by weight (water:composition) to about 10:1 by weight (water:composition).

UU. The composition of any of paragraphs BB-TT, wherein the perfume is at least 20% of the weight of the surfactant.

VV. Use of a rinse-off cleansing composition in any of claims BB-UU for enhancing fragrance of a rinse-off cleansing composition before use.

WW. Use of a rinse-off cleansing composition in any of claims BB-UU for enhancing in-vitro bloom of a rinse-off composition.

XX. Use of a rinse-off cleansing composition in any of claims BB-UU for enhancing fragrance of a rinse-off cleansing composition on skin or hair.

YY. Use of a rinse-off cleansing composition of any of claims BB-UU for enhancing fragrance longevity of a rinse-off cleansing composition on skin or hair.

ZZ. A liquid rinse-off personal cleansing composition, consisting essentially of: a) from 11% to 15%, by weight of the composition, of a surfactant, wherein the surfactant comprises from about 4% to about 10%, by weight of the composition, of a branched anionic surfactant, and from about 1% to about 9%, by weight of the composition, of a cosurfactant; b) from about 1.5% to about 5%, by weight of the composition, of a perfume; c) from about 1.5% to about 8%, by weight of the composition, of a hydric solvent comprising dipropylene glycol; d) from about 0.5% to about 4%, by weight of the composition, of hydroxypropylmethyl cellulose; e) from about 58% to about 93%, by weight of the composition, of water; and f) optionally, one or more addition ingredients comprising a dye, pH modifier, a preservative, or a combination thereof.

AAA. The composition of paragraph ZZ, wherein the composition comprises from about 10% to about 14%, by weight of the composition, of total surfactant.

BBB. The composition of paragraph ZZ-AAA, wherein the branched anionic surfactant comprises a sulfate, an alkyl ether sulfate, a sulfonate, a carboxylate, a sarcosinate, or a combination thereof.

CCC. The composition of paragraph ZZ-BBB, wherein the branched anionic surfactant comprises sodium trideceth-2 sulfate, sodium trideceth-3 sulfate, sodium laureth-1 sulfate, sodium laureth-2 sulfate, sodium laureth-3 sulfate, sodium cocoyl isethionate, or a combination thereof.

DDD. The composition of any of paragraphs ZZ-CCC, wherein the composition comprises from about 2% to about 7%, or from about 4% to about 8%, by weight of the composition, of the cosurfactant.

EEE. The composition of paragraph DDD, wherein the cosurfactant comprises a betaine.

FFF. The composition of paragraph DDD, wherein the cosurfactant comprises cocamidopropyl betaine.

GGG. The composition of any of paragraphs ZZ-FFF, wherein the composition comprises from about 1% to about 7%, from about 2% to about 7%, or from about 2% to about 6%, by weight of the composition, of the solvent.

HHH. The composition of any of paragraphs ZZ-GGG, wherein the composition comprises from about 1% to about 3%, by weight of the composition, of the thickener.

III. The composition of paragraph ZZ-HHH, wherein the hydroxypropylmethyl cellulose has a viscosity range of about 2,600 to about 90,000 cP.

JJJ. The composition of any of paragraphs ZZ-III, wherein the composition has a G' at 1 Hz of about 50 Pa to about 2500 Pa, from about 100 Pa to about 1500 Pa, or from about 150 Pa to about 1000 Pa.

KKK. The composition of any of paragraphs ZZ-JJJ, wherein the composition has a G" at 1 Hz of about 20 Pa to about 250 Pa, from about 35 Pa to about 200 Pa, from about 40 Pa to about 150 Pa; or from about 50 Pa to about 100 Pa.

LLL. The composition of any of paragraphs ZZ-KKK, wherein the composition has a viscosity at a shear rate of 0.10 l/sec of about 10 PaS to about 1200 PaS; from about 20 PaS to about 1000 PaS, from about 20 PaS to about 500 PaS, or from about 20 PaS to about 300 PaS, when measured in accordance with the Viscosity Method; and/or a viscosity a shear rate of 10 l/sec of about 1 PaS to about 30 PaS, from about 1 PaS to about 20 PaS, from about 1 PaS to about 15 PaS, or from about 1 PaS to about 10 PaS, when measured in accordance with the Viscosity Method.

MMM. The composition of any of paragraphs ZZ-LLL, wherein the composition is a microemulsion or contains a microemulsion.

NNN. The composition of any of paragraphs ZZ-MMM, wherein the composition is not in the form of a ringing gel.

OOO. The composition of any of paragraphs ZZ-NNN, wherein at least a portion of the composition becomes a microemulsion upon dilution with water of about 3:1 by weight (water:composition) to about 10:1 by weight (water:composition).

PPP. The composition of any of paragraphs ZZ-OOO, wherein the perfume is at least 20% of the weight of the surfactant.

QQQ. Use of a rinse-off cleansing composition in any of claims ZZ-PPP for enhancing fragrance of a rinse-off cleansing composition before use.

RRR. Use of a rinse-off cleansing composition in any of claims ZZ-PPP for enhancing in-vitro bloom of a rinse-off composition.

SSS. Use of a rinse-off cleansing composition in any of claims ZZ-PPP for enhancing fragrance of a rinse-off cleansing composition on skin or hair.

TTT. Use of a rinse-off cleansing composition of any of claims ZZ-PPP for enhancing fragrance longevity of a rinse-off cleansing composition on skin or hair.

EXAMPLES

The inventive examples are prepared by weighing the components together into a Speedmixer pot, stirring by hand briefly to homogenize the fluids, and then speedmixing for 60 seconds at 2750 rpm.

|  | Inv. Exp. 1 | Inv. Exp. 2 | Inv. Exp. 3 | Inv. Exp. 4 | Inv. Exp. 5 | Inv. Exp. 6 |
|---|---|---|---|---|---|---|
| water | QS | QS | QS | QS | QS | QS |
| Methocel 40-0101 | 1 | 1 | 1 | 1 | 1 | 1 |
| Cocamidopropyl betaine (30%) | 5.6 | 5.6 | 5.6 | 5.6 | — | 5.6 |
| Laurylamidopropyl betaine (30%) | — | — | — | — | 4.53 | — |
| Sodium trideceth 2 sulfate (65%) | 8.4 | 8.4 | 8.4 | 8.4 | 6.80 | 8.4 |
| Sodium myristate | — | — | — | — | 2 | — |
| EDTA | 0.1 | 0.1 | 0.1 | 0.1 | 0.1 | 0.1 |
| Sodium benzoate | 0.25 | 0.25 | 0.25 | 0.25 | 0.25 | 0.25 |
| Dipropylene glycol | 2.2 | — | — | 1.1 | 5.2 | — |
| Butylene glycol | — | 2.2 | — | — | — | — |
| Hexylene glycol | — | — | 2.2 | — | — | 2.2 |
| Propylene glycol | — | — | — | 1.1 | — | — |
| Citric acid | 0.14 | 0.14 | 0.14 | 0.14 | 0.45 | 0.14 |
| Perfume | 4 | 4 | 4 | 4 | 2 | 2 |
| Surfactant wt % of composition | 14 | 14 | 14 | 14 | 13.33 | 14 |
| Total GCMS headspace counts | 3,277,762 | 7,307,629 | 5,974,645 | 3,607,715 | 3,568,324 | 4,222,708 |
| G' at 1 Hz (Pa) | 521.5 | 412.2 | 390 | 435.5 | 259.6 | 30.7 |
| G" at 1 Hz (Pa) | 118 | 118.5 | 105.5 | 111.8 | 91.4 | 32.5 |
| Viscosity at 0.1 1/sec (Pa * s) | 309 | 205.3 | 163.2 | 248.1 | 61.3 | 24.3 |
| Viscosity at 10 1/sec (Pa * s) | 10.9 | 10.4 | 9.5 | 9.5 | 7.5 | 2 |

|  | Comparative Exp. 2 |
|---|---|
| water | QS |
| Methocel 40-0101 | — |
| Cocamidopropyl betaine (30%) | 1.2 |
| Sodium laureth 1 sulfate (26%) | 10.8 |
| EDTA | 0.1 |
| Sodium benzoate | 0.25 |
| Citric acid | 0.12 |
| Perfume | 1.2 |
| Surfactant wt % of composition | 12 |
| Total GCMS headspace counts | 1,558,616 |
| G' at 1 Hz (Pa) | 69.8 |
| G" at 1 Hz (Pa) | 122.5 |
| Viscosity at 0.1 1/sec (Pa * s) | 25.6 |
| Viscosity at 10 1/sec (Pa * s) | 11.5 |

Test Methods a) G' and G" Test Method

To measure the viscoelastic properties of a personal care composition, the viscous (G") and elastic (G') moduli, use a rheometer such as a AR G2 Rheometer (TA Instruments, DE, USA) with 1 degree cone upper geometry with a diameter of 40 mm and flat plate lower geometry with Peltier heating/cooling to control temperature. Place approximately 1 gram of personal care composition onto the lower test geometry and lower the upper geometry into position, lock the geometry and wipe away excess composition to create an even surface around the edge of the geometry. Conduct the oscillatory test over frequency range of 0.01 to 100 Hz, collecting 5 data points per decade, using a constant oscillatory stress of 0.5968 Pa and a set temperature of 25° C. The tan delta is calculated as the ratio of G"/G'.

Record the G' and G" (Pa) at a frequency of 1 Hz and 10 Hz.

b) Viscosity Method

To measure the viscosity of a personal care composition use a rheometer such as an AR G2 controlled stress Rheometer (TA Instruments, DE, USA) equipped with 1 degree cone upper geometry with a diameter of 40 mm and flat plate lower geometry equipped with Peltier heating/cooling to control temperature. Pipette approximately 1 gram of personal care composition onto the lower test geometry and lower the upper geometry into position, wipe away any excess composition to create an even surface around the edge of the geometry. Conduct a continuous flow test at 25° C., controlling the shear rate from 0.01 to 100 1/sec over a time period of 3 minutes, running the test in log mode and collecting 15 points per decade. Record the viscosity (Pa*s) at the shear rates of 0.10 1/sec, 1 1/sec, and 10 1/sec.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rinse-off cleansing composition delivering enhanced initial perfume perception, perfume bloom during cleansing, and perfume retention on the skin for many hours after cleansing, comprising:
   a. from 11% to 17%, by weight of the composition, of a surfactant, wherein the surfactant comprises from about 4% to about 10%, by weight of the composition, of a branched anionic surfactant, and from about 1% to about 9%, by weight of the composition, of a cosurfactant comprising a betaine;
   a. from 1.4% to about 5%, by weight of the composition, of a perfume, wherein the weight percent of perfume is from about 10% to about 90%, by weight of the surfactant;
   b. from about 1% to about 10%, by weight of the composition, of a hydric solvent comprising dipropylene glycol, wherein the weight percent of the hydric solvent is from about 8% to about 60%, by weight of the surfactant;
   c. from about 0.5% to about 6%, by weight of the composition, of a nonionic cellulose thickener; and
   d. from about 58% to about 93%, by weight of the composition, of water;
   f: a gel comprising a portion of the surfactant and the cellulose thickener;
   wherein the rinse-off cleansing composition has a G' at 1 Hz of about 25 Pa to about 3000 Pa;
   wherein the composition has a viscosity at a shear rate of 0.10 l/sec of about 20 PaS to about 300 PaS;
   wherein the composition spontaneously forms a microemulsion comprising at least a portion of the perfume upon aqueous dilution.

2. The rinse-off cleansing composition of claim 1, wherein the composition comprises from 11% to about 14%, by weight of the composition, of the surfactant.

3. The rinse-off cleansing composition of claim 1, wherein the branched anionic surfactant comprises a sulfate, an alkyl ether sulfate, a sulfonate, a carboxylate, a sarcosinate, or a combination thereof.

4. The rinse-off cleansing composition of claim 1, wherein the branched anionic surfactant comprises sodium trideceth-2 sulfate, sodium trideceth-3 sulfate, sodium laureth-1 sulfate, sodium laureth-2 sulfate, sodium laureth-3 sulfate, sodium cocoyl isethionate, or a combination thereof.

5. The rinse-off cleansing composition of claim 1, wherein the surfactant comprises from about 2% to about 7%, by weight of the composition, of a cosurfactant.

6. The rinse-off cleansing composition of claim 1, wherein the cosurfactant comprises cocamidopropyl betaine.

7. The rinse-off cleansing composition of claim 1, wherein the composition has from about 1.5% to about 8%, by weight of the composition, of the hydric solvent.

8. The rinse-off cleansing composition of claim 7, wherein the hydric solvent consists of dipropylene glycol.

9. The rinse-off cleansing composition of claim 1, wherein the thickener comprises hydroxypropylmethyl cellulose.

10. The rinse-off cleansing composition of claim 1, wherein the composition has a G' at 1 Hz of about 150 Pa to about 1000 Pa.

11. The rinse-off cleansing composition of claim 1, wherein the composition has a G" at 1 Hz of about 20 Pa to about 250 Pa.

12. The rinse-off cleansing composition of claim 1, wherein the composition is not a ringing gel.

13. The rinse-off cleansing composition of claim 1, wherein the perfume is at least 20% of the weight of the surfactant.

14. A liquid rinse-off cleansing composition delivering enhanced initial perfume perception, perfume bloom during cleansing, and perfume retention on the skin for many hours after cleansing, comprising:
   b. from 11% to 15%, by weight of the composition, of a surfactant, wherein the surfactant comprises from about 4% to about 10%, by weight of the composition, of a branched anionic surfactant selected from the group consisting of sodium trideceth-2 sulfate, sodium trideceth-3 sulfate, sodium laureth-1 sulfate, sodium laureth-2 sulfate, sodium laureth-3 sulfate, sodium cocoyl isethionate, and a combination thereof, and from about 4% to about 8%, by weight of the composition, of a cosurfactant comprising an alkyl amidopropyl betaine;
   c. from about 1.5% to about 5%, by weight of the composition, of a perfume, wherein the weight percent of perfume is from about 10% to about 90%, by weight of the surfactant;
   d. from about 1.5% to about 8%, by weight of the composition, of a hydric solvent consisting of dipropylene glycol, dibutylene glycol, or a combination thereof;
   e. from about 0.1% to about 4%, by weight of the composition, of a water soluble polymeric thickener; and
   f. from about 58% to about 93%, by weight of the composition, of water;
   g. a gel comprising a portion of the surfactant and the cellulose thickener;
   wherein the composition has a viscosity at a shear rate of 0.10 l/sec of about 20 PaS to about 300 PaS;
   wherein the composition spontaneously forms a microemulsion comprising at least a portion of the perfume upon aqueous dilution.

15. The liquid rinse-off cleansing composition of claim 14, wherein the cosurfactant comprises cocamidopropyl betaine.

16. The liquid rinse-off cleansing composition of claim 14, wherein the thickener comprises hydroxypropyl methylcellulose.

17. The liquid rinse-off cleansing composition of claim 14, wherein the composition is not a ringing gel.

18. A liquid rinse-off personal cleansing composition delivering enhanced initial perfume perception, perfume bloom during cleansing, and perfume retention on the skin for many hours after cleansing, consisting essentially of:
   a. from about 5% to 15%, by weight of the composition, of a surfactant, wherein the surfactant comprises from about 4% to about 10%, by weight of the composition, of a branched anionic surfactant selected from the group consisting of sodium trideceth-2 sulfate, sodium trideceth-3 sulfate, sodium laureth-1 sulfate, sodium laureth-2 sulfate, sodium laureth-3 sulfate, sodium cocoyl isethionate, and a combination thereof, and from about 1% to about 9%, by weight of the composition, of a cosurfactant;

b. from about 1.5% to about 5%, by weight of the composition, of a perfume, wherein the weight percent of perfume is from about 10% to about 90%, by weight of the surfactant;

c. from about 1.5% to about 8%, by weight of the composition, of a hydric solvent comprising dipropylene glycol;

d. from about 0.5% to about 4%, by weight of the composition, of hydroxypropylmethyl cellulose;

e. from about 58% to about 93%, by weight of the composition, of water; and f. optionally, one or more addition ingredients comprising a dye, pH modifier, a preservative, or a combination thereof;

g. a gel comprising a portion of the surfactant and the cellulose thickener;

wherein the composition has a viscosity at a shear rate of 0.10 1/sec of about 20 PaS to about 300 PaS;

wherein the composition spontaneously forms a microemulsion comprising at least a portion of the perfume upon aqueous dilution.

19. The liquid rinse-off cleansing composition of claim 4 wherein the branched anionic surfactant comprises sodium tridecth-2 sulfate.

20. The liquid rinse-off cleansing composition of claim 14 wherein the branched anionic surfactant comprises sodium tridecth-2 sulfate.

21. The liquid rinse-off cleansing composition of claim 18 wherein the branched anionic surfactant comprises sodium tridecth-2 sulfate.

* * * * *